United States Patent [19]

Prezewowsky et al.

[11] 4,259,325

[45] Mar. 31, 1981

[54] 1,3-DIBENZOIC ACID ESTERS OF 17α-ETHYNYL-7α-METHYL-1,3,5(10)-ESTRATRIENE-1,3,17β-TRIOL

[75] Inventors: Klaus Prezewowsky; Hermann Steinbeck; Rudolf Wiechert, all of Berlin, Fed. Rep. of Germany

[73] Assignee: Schering Aktiengesellschaft (A.G.), Berlin and Bergkamen, Fed. Rep. of Germany

[21] Appl. No.: 28,744

[22] Filed: Apr. 10, 1979

[30] Foreign Application Priority Data

Apr. 21, 1978 [DE] Fed. Rep. of Germany ....... 2818164

[51] Int. Cl.³ .................. C07J 1/00; A61K 31/56
[52] U.S. Cl. .................. 424/238; 260/397.5; 424/240

[58] Field of Search ............... 424/238, 240; 260/397.5

[56] References Cited

U.S. PATENT DOCUMENTS

| | | | |
|---|---|---|---|
| 3,024,256 | 3/1962 | Jiu ........................... | 260/397.4 |
| 3,310,470 | 3/1967 | Schulze et al. ............ | 424/238 |
| 3,574,197 | 4/1971 | Prezewowsky et al. ..... | 260/239.55 |
| 3,951,959 | 4/1976 | Prezewowsky et al. ..... | 260/397.5 |

*Primary Examiner*—Elbert L. Roberts
*Attorney, Agent, or Firm*—Millen & White

[57] ABSTRACT

1,3-Dibenzoic acid esters of 17α-ethynyl-7α-methyl-1,3,5(10)-estratriene-1,3,17β-triol possess strong estrogenic and ovulation-inhibiting activities. As compared to the corresponding diacetic acid ester, these dibenzoic acid esters remain stable over 2-7 months even in the desired, low dosage at a thermal load of up to 60° C.

12 Claims, No Drawings

1,3-DIBENZOIC ACID ESTERS OF 17α-ETHYNYL-7α-METHYL-1,3,5(10)-ESTRA-TRIENE-1,3,17β-TRIOL

BACKGROUND OF THE INVENTION

The present invention relates to highly active and stable esters of 17α-ethynyl-7α-methyl-1,3,5(10)-estratriene-1,3,17β-triol, to processes for the preparation thereof and to pharmaceutical compositions containing the same.

German Pat. No. 1,593,509 discloses 1-hydroxy-7α-methylestradiol derivatives of the general formula

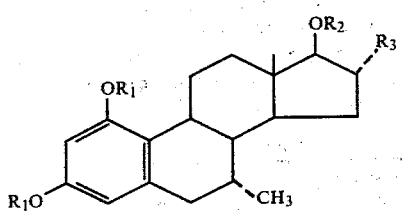

wherein
- $R_1$ and $R_2$, which can be the same or different, are hydrogen, lower alkyl, a saturated oxygen-heterocyclic residue, or a physiologically acceptable acid residue, and
- $R_3$ is hydrogen or saturated or unsaturated lower alkyl.

These compounds possess valuable therapeutic properties. They are distinguished, in particular, by strong estrogenic and ovulation-inhibiting activities. A preferred compound of the German patent is 17α-ethynyl-1,3-diacetoxy-7α-methyl-1,3,5(10)estratrien-17β-ol (I). During clinical testing also, it proved to be a very strong estrogen for its effectiveness on the endometrium. Compared to 17α-ethynylestradiol, compound I has an activity which is about 10 times higher.

With such highly effective active agents, correspondingly low doses only need be used in preparations. Accordingly, and unfortunately, especially high stabilities are required of the active agents. It has now been found that compound I, in the desired, low dosage in which it is used in a preparation, i.e., 0.001–0.05 mg, is unstable during exertion of a dry temperature load of up to 60° C. over a period of 2–7 months.

Consequently, it is desired to have a highly effective such agent which also has high stability, e.g., storage stability.

SUMMARY OF THE INVENTION

Accordingly, it is an object of the invention to provide estrogenically highly active compounds which also possess high stability.

Upon further study of the specification and appended claims, further objects and advantages of this invention will become apparent to those skilled in the art.

These objects have been attained by providing 1,3-dibenzoic acid esters of 17α-ethynyl-7α-methyl-1,3,5(10)-estratrien-1,3,17β-triol, especially 17α-ethynyl-1,3-dibenzoyloxy-7α-methyl-1,3,5(10)-estratrien-17β-ol.

DETAILED DISCUSSION

Surprisingly, these 1,3-dibenzoic acid esters remain stable under the same thermal load mentioned above with regard to compound I. Furthermore, the benzoic acid esters of this invention have approximately the same advantageous activity as the 1,3-diacetate (I). They are not described in German Pat. No. 1,593,509.

Suitable benzoic acid esters of this invention include the esters of unsubstituted benzoic acid as well as the equivalent esters of benzoic acid having a substituted phenyl nucleus. Suitable such equivalent substituents include chlorine, methyl, hydroxy, amino and methoxy. More generically, other equivalent substituents include bromine, iodine, ethyl and ethoxy. Preferably, one or two of such substituents are present. The unsubstituted 1,3-dibenzoic acid ester is especially preferred.

The preparation of the novel dibenzoic acid esters can be effected according to methods known per se. Thus, a starting material of 17α-ethynyl-7α-methyl-1,3,5(10)-estratrien-1,3,17β-triol, described in German Pat. No. 1,593,509 can be conventionally esterified at its free hydroxy groups in the 1- and 3-positions by the desired benzoic acid or a reactive derivative thereof. Preferred such reactive derivatives are the anhydrides and halogenides, especially the chloride. To avoid a simultaneous esterification of the tertiary 17-hydroxy group, the esterification is preferably conducted in the presence of a base, such as, for example, pyridine, at room temperature.

The novel dibenzoic acid esters possess strong estrogenic and ovulation-inhibiting activities in mammals, including humans. They can be conventionally formulated with one or more pharmaceutical vehicles or diluents, optionally with the addition of progestogens, into stable preparations, e.g., tablets, dragees, capsules, solutions, ointments, etc. The effective agent concentration in the pharmaceutical compositions is dependent on the form of application and the field of use. Thus, for example, capsules or tablets for the treatment of gynecological disturbances may contain 0.001–0.05 mg of active ingredient; oily solutions for intramuscular injection may contain, per milliliter, about 0.01–0.1 mg of active ingredient; and vaginal ointments may contain about 0.1–10 mg per 100 ml of ointment.

For female contraceptives, the estrogens of this invention are utilized in combination with conventional progestogens. Tablets or dragees for daily ingestion of one tablet or of one dragee contain preferably 0.003–0.05 mg of the estrogen of this ivention and 0.05–0.5 mg of a progestogen.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight.

EXAMPLE 1

A solution of 2.4 g. of 17α-ethynyl-7α-methyl1,3,5(10)-estratriene-1,3,17β-triol (German Pat. No. 1,593,509) in 28 ml. of pyridine is combined under ice cooling and a protective gas dropwise with 5 ml. of benzoyl chloride and agitated for 40 minutes at 0° C. The batch is thereafter introduced into ice water/sodium chloride, and the oily crude product is obtained as the remainder of a decanting step; this crude product is dissolved in ether. The ether solution is washed with water, dried, and worked up. The crude product is purified by chromatography and recrystallized from cyclohexane, thus obtaining 2.7 g of 17α-ethynyl-1,3-dibenzoyloxy-7α-methyl-1,3,5(10)-estratrien-17β-ol, m.p. 109°–110° C. (under decomposition).

EXAMPLE 2

0.003 g. of 17α-ethynyl-1,3-dibenzoyloxy-7α-methyl1,3,5(10)-estratrien-17β-ol and 209.997 g. of lactose are mixed homogeneously, and respectively 210 mg. of this mixture is filled into hard-gelatin separable capsules of size No. 3.

EXAMPLE 3

0.010 g. of 17α-ethynyl-1,3-dibenzoyloxy-7α-methyl1,3,5(10)-estratrien-17β-ol and 209.990 g. of lactose are mixed homogeneously, and respectively 210 mg. of this mixture is filled into hard-gelatin separable capsules of size No. 3.

EXAMPLE 6

Comparative stability tests on 17α-ethynyl-1,3-diacetoxy-7α-methyl-1,3,5(10)-estratrien-17β-ol (I) and 17α-ethynyl-1,3-dibenzoyloxy-7α-methyl-1,3,5(10)-estratrien-17β-ol (II).

Preparation of Powder Mixtures

A: The active agent is dissolved in methylene chloride and applied to lactose, whereafter the methylene chloride is evaporated.

B: Micronized active agent is triturated with lactose.

Active agent concentrations: 1%; 0.01%; 0.003%.

Storage in brown glass jars at room temperature (Rt) (22° C.), at 40° C.; 50° C.; and 60° C.

Results of the potency determination of diacetate I and dibenzoate II (see table).

The potency percentage values by weight listed in the Table were determined by quantitative thin layer chromatography.

TABLE

|  | 2 Months | | | | 7 Months | | | |
| --- | --- | --- | --- | --- | --- | --- | --- | --- |
|  | Rt | 40° C. | 50° C. | 60° C. | Rt | 40° C. | 50° C. | 60° C. |
| Preparation A | | | | | | | | |
| Diacetate I | | | | | | | | |
| 1% | 94% | 94% | 94% | 94% | 95% | 95% | 95% | 92% |
| 0.01% | 100% | 90% | 87% | 48% | 95% | 83% | 55% | 0% |
| 0.003% | 99% | 98% | 74% | 34% | 96% | 55% | 0% | 0% |
| Dibenzoate II | | | | | | | | |
| 1% | 95% | 98% | 104% | 100% | 104% | 105% | 104% | 96% |
| 0.01% | 95% | 104% | 95% | 98% | 102% | 100% | 95% | 105% |
| 0.003% | 97% | 105% | 104% | 96% | 104% | 105% | 95% | 89% |
| Preparation B | | | | | | | | |
| Diacetate I | | | | | | | | |
| 1% | 98% | 96% | 102% | 104% | 98% | 96% | 96% | 94% |
| 0.01% | 100% | 84% | 73% | 70% | 100% | 77% | 50% | 46% |
| 0.003% | 99% | 75% | 60% | 29% | 92% | 68% | 23% | 0% |
| Dibenzoate II | | | | | | | | |
| 1% | 99% | 102% | 101% | 105% | 97% | 100% | 103% | 104% |
| 0.01% | 105% | 102% | 99% | 98% | 103% | 101% | 102% | 95% |
| 0.003% | 105% | 103% | 102% | 100% | 99% | 96% | 95% | 88% |

EXAMPLE 4

Tablets can be prepared in the usual way from the following ingredients:

| | |
| --- | --- |
| 0.010 mg. | 17 α-ethynyl-1,3-dibenzoyloxy-7α-methyl-1,3,5(10)-estratrien-17β-ol |
| 0.100 mg. | 17 α-ethynyl-17β-hydroxy-18-methyl-4-estren-3-one (Levonorgestrel) |
| 55.290 mg. | lactose |
| 24.000 mg. | microcrystalline cellulose |
| 0.600 mg. | magnesium stearate |
| 80.000 mg. | total weight of tablet |

EXAMPLE 5

Composition of another tablet:

| | |
| --- | --- |
| 0.010 mg. | 17 α-ethynyl-1,3-dibenzoyloxy-7α-methyl-1,3,5(10)-estratrien-17β-ol |
| 0.075 mg. | 17 α-ethynyl-17β-hydroxy-18-methyl-4,15-estradien-3-one |
| 55.315 mg. | mannitol |
| 24.000 mg. | microcrystalline cellulose |
| 0.600 mg. | magnesium stearate |
| 80.000 mg. | total weight of tablet |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. The 1,3-dibenzoic acid ester of 17α-ethynyl-7α-methyl-1,3,5(10)—estratrien-1,3,17β-triol, and the corresponding esters wherein the phenyl ring of the benzoic acid residue is substituted by chlorine, bromine, iodine, methyl, ethyl, hydroxy, amino, methoxy or ethoxy.

2. 17α-Ethynyl-1,3-dibenzoyloxy-7α-methyl-1,3,5(10)-estratrien-17β-ol.

3. A pharmaceutical composition comprising an estrogenically effective amount of a compound of claim 1 and a pharmaceutically acceptable carrier.

4. The composition of claim 3, wherein the active compound is 17α-ethynyl-1,3-dibenzoyloxy-7α-methyl-1,3,5(10)-estratrien-17β-ol.

5. A method of achieving estrogenic effects in a mammal which comprises administering to the mammal an estrogenically effective amount of a compound of claim 1.

6. The method of claim 5 wherein the compound administered is 17α-ethynyl-1,3-dibenzoyloxy-7α-methyl-1,3,5(10)-estratrien-17β-ol.

7. A method of inhibiting ovulation in a mammal which comprises administering to the mammal an amount of a compound of claim 1 effective to inhibit ovulation.

8. The method of claim 7 wherein the compound administered is 17α-ethynyl-1,3-dibenzoyloxy-7α-methyl-1,3,5(10)-estratrien-17β-ol.

9. The composition of claim 3 which further comprises a progestationally effective amount of a protestogen.

10. The composition of claim 4 which further comprises a progestationally effective amount of a progestogen.

11. The composition of claim 3, wherein the amount of estrogenic ingredient is 0.01–0.003 wt.%.

12. The composition of claim 4, wherein the amount of estrogenic ingredient is 0.01–0.003 wt.%.

* * * * *